(12) United States Patent
Melville et al.

(10) Patent No.: US 7,680,373 B2
(45) Date of Patent: Mar. 16, 2010

(54) TEMPERATURE ADJUSTMENT IN SCANNING BEAM DEVICES

(75) Inventors: Charles David Melville, Issaquah, WA (US); Richard S. Johnston, Sammamish, WA (US)

(73) Assignee: University of Washington, Seattle, WA (US)

( * ) Notice: Subject to any disclaimer, the term of this patent is extended or adjusted under 35 U.S.C. 154(b) by 162 days.

(21) Appl. No.: 11/521,523

(22) Filed: Sep. 13, 2006

(65) Prior Publication Data

US 2008/0073517 A1    Mar. 27, 2008

(51) Int. Cl.
G02B 6/32       (2006.01)
(52) U.S. Cl. .................................. 385/33; 2/94
(58) Field of Classification Search .................. 385/33, 385/31, 91
See application file for complete search history.

(56) References Cited

U.S. PATENT DOCUMENTS

| | | | |
|---|---|---|---|
| 3,470,320 A | 9/1969 | Pike et al. | |
| 3,644,725 A | 2/1972 | Lochridge, Jr. | |
| 4,206,495 A | 6/1980 | McCaslin | |
| 4,234,788 A | 11/1980 | Palmer et al. | |
| 4,264,208 A | 4/1981 | Haberl et al. | |
| 4,710,619 A | 12/1987 | Haberl | |
| 4,743,283 A | 5/1988 | Borsuk | |
| 4,768,513 A | 9/1988 | Suzuki | |
| 4,770,185 A | 9/1988 | Silverstein et al. | |
| 4,782,228 A | 11/1988 | Westell | |
| 4,821,117 A | 4/1989 | Sekiguchi | |
| 4,831,370 A | 5/1989 | Smoot | |
| 4,872,458 A | 10/1989 | Kanehira et al. | |
| 4,948,219 A | 8/1990 | Seino et al. | |
| 4,963,018 A | 10/1990 | West | |
| 5,081,350 A | 1/1992 | Iwasaki et al. | |
| 5,172,685 A | 12/1992 | Nudelman | |
| 5,178,130 A | 1/1993 | Kaiya | |
| 5,185,835 A | 2/1993 | Vial et al. | |
| 5,315,383 A | 5/1994 | Yabe et al. | |
| 5,360,968 A | 11/1994 | Scott | |
| 5,454,807 A | 10/1995 | Lennox et al. | |

(Continued)

FOREIGN PATENT DOCUMENTS

EP    1077360    2/2001

(Continued)

OTHER PUBLICATIONS

"PCT/US2007/009598 International Search Report", (Jan. 3, 2008), 3 pages.

(Continued)

*Primary Examiner*—Frank G Font
*Assistant Examiner*—Eric Wong
(74) *Attorney, Agent, or Firm*—Blakely, Sokoloff, Taylor & Zafman LLP

(57) ABSTRACT

Scanning beam devices are disclosed. In one aspect, an apparatus may include a housing having a transparent portion. A scanning optical element may be enclosed within the housing. Light may be directed between the scanning optical element and the transparent portion of the housing. The device may include a temperature adjustment device to adjust a temperature within the housing. Methods of using such apparatus are also disclosed, as are base stations to control the adjustment of the temperature.

23 Claims, 9 Drawing Sheets

U.S. PATENT DOCUMENTS

| | | | |
|---|---|---|---|
| 5,455,669 A | 10/1995 | Wetteborn | |
| 5,459,570 A | 10/1995 | Swanson et al. | |
| 5,557,444 A | 9/1996 | Melville et al. | |
| 5,596,339 A | 1/1997 | Furness, III et al. | |
| 5,627,922 A | 5/1997 | Koelman et al. | |
| 5,664,043 A | 9/1997 | Donaldson et al. | |
| 5,694,237 A | 12/1997 | Melville | |
| 5,695,491 A | 12/1997 | Silverstein | |
| 5,701,132 A | 12/1997 | Kollin et al. | |
| 5,751,465 A | 5/1998 | Melville et al. | |
| 5,784,098 A | 7/1998 | Shoji et al. | |
| 5,822,073 A | 10/1998 | Yee et al. | |
| 5,822,486 A | 10/1998 | Svetkoff et al. | |
| 5,887,009 A | 3/1999 | Mandella et al. | |
| 5,894,122 A | 4/1999 | Tomita | |
| 5,903,397 A | 5/1999 | Melville et al. | |
| 5,913,591 A | 6/1999 | Melville | |
| 5,939,709 A | 8/1999 | Ghislain et al. | |
| 5,969,871 A | 10/1999 | Tidwell et al. | |
| 5,982,528 A | 11/1999 | Melville | |
| 5,982,555 A | 11/1999 | Melville et al. | |
| 5,991,048 A | 11/1999 | Karlson et al. | |
| 5,995,264 A | 11/1999 | Melville | |
| 6,046,720 A | 4/2000 | Melville et al. | |
| 6,049,407 A | 4/2000 | Melville | |
| 6,061,163 A | 5/2000 | Melville | |
| 6,069,698 A | 5/2000 | Ozawa et al. | |
| 6,069,725 A | 5/2000 | Melville | |
| 6,097,353 A | 8/2000 | Melville et al. | |
| 6,154,321 A | 11/2000 | Melville et al. | |
| 6,157,352 A | 12/2000 | Kollin et al. | |
| 6,166,841 A | 12/2000 | Melville | |
| 6,191,761 B1 | 2/2001 | Melville et al. | |
| 6,204,832 B1 | 3/2001 | Melville et al. | |
| 6,220,711 B1 | 4/2001 | Melville et al. | |
| 6,243,186 B1 | 6/2001 | Melville et al. | |
| 6,257,727 B1 | 7/2001 | Melville | |
| 6,263,234 B1 | 7/2001 | Engelhardt et al. | |
| 6,281,862 B1 | 8/2001 | Tidwell et al. | |
| 6,285,505 B1 | 9/2001 | Melville et al. | |
| 6,288,816 B1 | 9/2001 | Melville et al. | |
| 6,291,819 B1 | 9/2001 | Hartley | |
| 6,294,775 B1 | 9/2001 | Seibel et al. | |
| 6,317,548 B1 | 11/2001 | Rockwell et al. | |
| 6,369,953 B2 | 4/2002 | Melville et al. | |
| 6,388,641 B2 | 5/2002 | Tidwell et al. | |
| 6,411,838 B1 | 6/2002 | Nordstrom et al. | |
| 6,441,359 B1 | 8/2002 | Cozier et al. | |
| 6,492,962 B2 | 12/2002 | Melville et al. | |
| 6,535,183 B2 | 3/2003 | Melville et al. | |
| 6,538,625 B2 | 3/2003 | Tidwell et al. | |
| 6,560,028 B2 | 5/2003 | Melville et al. | |
| 6,563,105 B2 | 5/2003 | Seibel et al. | |
| 6,581,445 B1 * | 6/2003 | Weiss | 73/75 |
| 6,627,903 B1 | 9/2003 | Hirayanagi | |
| 6,700,552 B2 | 3/2004 | Kollin et al. | |
| 6,734,835 B2 | 5/2004 | Tidwell et al. | |
| 6,747,753 B1 | 6/2004 | Yamamoto | |
| 6,845,190 B1 | 1/2005 | Smithwick et al. | |
| 6,850,673 B2 | 2/2005 | Johnston, II et al. | |
| 6,856,712 B2 | 2/2005 | Fauver et al. | |
| 6,867,753 B2 | 3/2005 | Chinthammit et al. | |
| 6,959,130 B2 | 10/2005 | Fauver et al. | |
| 6,975,898 B2 | 12/2005 | Seibel | |
| 6,977,631 B2 | 12/2005 | Melville et al. | |
| 7,068,878 B2 | 6/2006 | Crossman-Bosworth et al. | |
| 7,123,790 B2 | 10/2006 | Rosman et al. | |
| 7,159,782 B2 | 1/2007 | Johnston et al. | |
| 7,184,150 B2 | 2/2007 | Qualing et al. | |
| 7,189,961 B2 | 3/2007 | Johnston et al. | |
| 7,230,583 B2 | 6/2007 | Tidwell et al. | |
| 7,252,236 B2 | 8/2007 | Johnston et al. | |
| 7,277,819 B2 * | 10/2007 | Marcus et al. | 702/170 |
| 2001/0051761 A1 | 12/2001 | Khadem | |
| 2001/0055462 A1 | 12/2001 | Seibel | |
| 2002/0062061 A1 | 5/2002 | Kaneko et al. | |
| 2002/0064341 A1 | 5/2002 | Fauver et al. | |
| 2002/0093467 A1 | 7/2002 | Tidwell et al. | |
| 2002/0093563 A1 | 7/2002 | Cline et al. | |
| 2002/0097498 A1 | 7/2002 | Melville et al. | |
| 2002/0139920 A1 | 10/2002 | Seibel et al. | |
| 2003/0004412 A1 | 1/2003 | Izatt et al. | |
| 2003/0010825 A1 | 1/2003 | Schmidt et al. | |
| 2003/0010826 A1 | 1/2003 | Dvorkis et al. | |
| 2003/0016187 A1 | 1/2003 | Melville et al. | |
| 2003/0048540 A1 * | 3/2003 | Xie et al. | 359/637 |
| 2003/0142042 A1 | 7/2003 | Tidwell et al. | |
| 2003/0169966 A1 * | 9/2003 | Tokizaki | 385/31 |
| 2003/0202361 A1 | 10/2003 | Johnston et al. | |
| 2004/0061072 A1 | 4/2004 | Gu et al. | |
| 2004/0122328 A1 | 6/2004 | Wang et al. | |
| 2004/0153030 A1 | 8/2004 | Novak et al. | |
| 2004/0196213 A1 | 10/2004 | Tidwell et al. | |
| 2004/0212851 A1 | 10/2004 | Osakabe | |
| 2004/0254474 A1 | 12/2004 | Seibel et al. | |
| 2005/0020926 A1 | 1/2005 | Wiklof et al. | |
| 2005/0025368 A1 | 2/2005 | Glukhovsky | |
| 2005/0085708 A1 | 4/2005 | Fauver et al. | |
| 2005/0085721 A1 | 4/2005 | Fauver et al. | |
| 2005/0174610 A1 | 8/2005 | Fukawa | |
| 2005/0182295 A1 | 8/2005 | Soper et al. | |
| 2005/0238277 A1 | 10/2005 | Wang et al. | |
| 2006/0072843 A1 | 4/2006 | Johnston | |
| 2006/0072874 A1 | 4/2006 | Johnston | |
| 2006/0077121 A1 | 4/2006 | Melville et al. | |
| 2006/0138238 A1 | 6/2006 | Johnston et al. | |
| 2006/0149134 A1 | 7/2006 | Soper et al. | |
| 2006/0186325 A1 | 8/2006 | Johnston et al. | |
| 2006/0195014 A1 | 8/2006 | Seibel et al. | |
| 2006/0226231 A1 | 10/2006 | Johnston et al. | |
| 2006/0287647 A1 | 12/2006 | Torchia et al. | |
| 2007/0081168 A1 | 4/2007 | Johnston et al. | |
| 2007/0091426 A1 | 4/2007 | Johnston et al. | |
| 2007/0129601 A1 | 6/2007 | Johnston et al. | |
| 2007/0135693 A1 * | 6/2007 | Melman et al. | 600/316 |
| 2007/0156021 A1 | 7/2007 | Morse et al. | |
| 2007/0273930 A1 | 11/2007 | Berier et al. | |

FOREIGN PATENT DOCUMENTS

| | | |
|---|---|---|
| EP | 1360927 | 11/2003 |
| EP | 1864606 | 12/2006 |
| GB | 2057709 | 4/1981 |
| GB | 2378259 | 2/2003 |
| JP | 08211313 | 8/1996 |
| WO | WO-9300551 | 1/1993 |
| WO | WO-0174266 | 10/2001 |
| WO | WO-03019661 | 3/2003 |
| WO | WO-2004/040267 | 5/2004 |
| WO | WO-2004040267 | 5/2004 |
| WO | WO-2004068218 | 8/2004 |
| WO | WO-2005009513 | 2/2005 |
| WO | WO-2006004743 | 1/2006 |
| WO | WO-2006041452 | 4/2006 |
| WO | WO2006041452 A1 | 4/2006 |
| WO | WO-2006041459 | 4/2006 |
| WO | WO-2006071216 | 7/2006 |
| WO | WO-2006096155 | 9/2006 |
| WO | WO-2006/106853 | 10/2006 |
| WO | WO-2006124800 | 11/2006 |
| WO | WO-2007070831 | 6/2007 |

| | | |
|---|---|---|
| WO | WO-2008/033168 | 3/2008 |

OTHER PUBLICATIONS

Brown, Christopher M., et al., "Optomechanical design and fabrication of resonant microscanners for a scanning fiber endoscope", *Optical Engineering,* vol. 45, XP002469237, (Apr. 2006), pp. 1-10.

Smithwick, Y. J., et al., "An error space controller for a resonating fiber scanner: simulation and implementation", *Journal of Dynamic Systems, Measurement and Control, Fairfiled, N.J., U.S.,* vol. 128, No. 4, XP009095153, ISSN: 0022-0434, (Dec. 2006), pp. 899-913.

Barhoum, Erek S., et al., "Optical modeling of an ultrathin scanning fiber endoscope, a preliminary study of confocal versus non-confocal detection", Optics Express, vol. 13, No. 19, (Sep. 8, 2005),7548-7562.

Brown, Christopher, et al., "A Novel Design for a Scanning Fiberoptic Endoscope", Human Interface Technology Laboratory, University of Washington, Seattle, WA 98195, One page.

Brown, Christopher M., et al., "Mechanical Design and Analysis for a Scanning Fiber Endoscope", Proceedings of 2001 ASME Int'l Mechanical Engineering Congress and Exposition, BED-vol. 51, (Nov. 11-16, 2001),165-166.

Chen, Tailian, et al., "Experiment of Coalescence of Dual Bubbles on Micro Heaters", Department of Mechanical Engineering, University of Florida, Gainesville, FL 32611-6300. USA., Printed from the Internet Aug. 13, 2006,1-10.

Fauver, Mark, et al., "Microfabrication of fiber optic scanners", (2002) In Proceedings of Optical Scanning II, SPIE 4773, pp. 102-110, 9 pages.

Johnston, Richard S., et al., "Scanning fiber endoscope prototype performance", Optical Fibers and Sensors for Medical Applications II, Proc. SPIE, vol. 4616, (Oct. 13, 2004),173-179.

Seibel, Eric J., et al., "Microfabricated optical fiber with microlens that produces large field-of-view, video rate, optical beam scanning for microendoscopy applications", Optical Fibers and Sensors for Medical Applications III, Proceedings of SPIE vol. 4957, (2003),46-55.

Seibel, Eric J., et al., "Modeling optical fiber dynamics for increased efficiencies in scanning fiber applications", Optical Fibers and Sensors for Medical Applications V, proceedings of SPIE vol. 5691, (2005),42-53.

Seibel, Eric J., et al., "P-37: Optical fiber scanning as a microdisplay source for a wearable low vision aid", Society for Information Display SID 2002, Boston, MA, (May 19-24, 2002),1-4.

Seibel, Eric J., et al., "Prototype scanning fiber endoscope", Optial Fibers and Sensors for Medical Applications II, Proc. of SPIE, vol. 4616, (2002),1-7.

Seibel, Eric J., et al., "Single fiber flexible endocope: general design for small size, high resoljution, and wide field of view", Human Interface Technology Laboratory, College of Engineering, University of Washington, Seattle, WA, 11 pages.

Seibel, Eric J., et al., "Ultrathin laser scanning bronchoscope and guidance system for the peripheral lung", 11th World Conference on Lung Cancer, (2005), P-178.

Seibel, Quinn Y., et al., "Unique Features of Optical Scanning, Single Fiber Endoscopy", Lasers in Surgery and Medicine 30, (2002),177-183.

Seibel, Eric, et al., "Unique Features of Scanning Fiber Optical Endopscopy", 2000 Annual Fall Meeting Abstracts T4.57, (2000),1.

Siebel, Eric J., et al., "A full-color scanning fiber endoscope", Optical Fibers and Sensors for Medical Diagnosis and Treatment Applications. Ed. I Gannot. Proc. SPIE vol. 6083, (2006),9-16.

Smithwick, Quinn Y., et al., "54,3: Modeling and Control of the Resonant Fiber Scanner for Laser Scanning Display or Acquisition", Department of Aeronautics and Astronautics, University of Washington, Seattle, WA SID 03 Digest, (2003),1455-1457.

Smithwick, Quinn Y., et al., "A Nonlinear State-Space Model of a Resonating Single Fiber Scanner for Tracking Control: Theory and Experiment", Transactions fo the ASME, vol. 126, (Mar. 2004),88-101.

Smithwick, Quinn Y., et al., "Control Aspects of the Single Fiber Scanning Endoscope", (2001) SPIE Optical Fibers and Sensors for Medical Applications, 4253, 176-188., 15 pages.

Smithwick, Quinn Y., et al., "Depth Enhancement using a Scanning Fiber Optical Endoscope", Department of Aeronautics, Human Interface Technology Laboratory, University of Washington, Seattle, Washington, 12 pages.

Tuttle, Brandon W., et al., "Delivery of therapeutic laser light using a singlemode silica fiber for a scanning fiber endoscope system", Optical Fibers and Sensors for Medical Diagnostics and Treatment Applications VI, Proc. of SPIE vol. 6083,, (2006),608307-1 to608307-12.

Wang, Wei-Chih, et al., "Development of an Optical Waveguide Cantilever Scanner", Opto-Ireland 2002: Optics and Photonics Technologies and Applications, Proceedings of SPIE vol. 4876 (2003), (2003),72-83.

Wang, Wei-Chih, et al., "Micromachined opital waveguide cantilever as a resonant optical scanner", Department of Mechanical Engineering, University of Washington, Seattle, WA 98195, Sensors and Actuators A 102, (2002),165-175.

Aloisi et al, "Electronic Linearization of Piezoelectric Actuators and Noise Budget in Scanning Probe Mircoscopy", Review of Scientific Instruments, vol. 77, No. 7, Jul. 5, 2006, pp. 073701-1 through 073701-6.

\* cited by examiner

TEMPERATURE ADJUSTMENT IN SCANNING BEAM DEVICES

BACKGROUND

1. Field

Embodiments of the invention relate to scanning beam devices. In particular, embodiments of the invention relate to temperature adjustment in scanning beam devices.

2. Background Information

Scanning beam devices are well known in the arts. Various example scanning beam devices are disclosed in at least the following references:

U.S. Pat. App. Pub. No. 20060138238 (Johnston et al.);
U.S. Pat. App. Pub. No. 20060072843 (Johnston);
U.S. Pat. App. Pub. No. 20060072874 (Johnston);
U.S. Pat. App. Pub. No. 20020064341. (Fauver et al.);
U.S. Pat. No. 6,563,105 (Seibel et al.);
U.S. Pat. No. 6,975,898 (Siebel);
U.S. Pat. No. 6,294,775 (Seibel et al.); and
"A Full-Color Scanning Fiber Endoscope", by Siebel et al., in Optical Fibers and Sensors for Medical Diagnosis and Treatment Applications, Ed. I. Gannot, Proc., SPIE vol. 6083: 9-16 (2006).

These are just a few examples. Other examples of scanning beam devices are described in the patent and general literature.

One type of scanning beam device is a scanning fiber device. The scanning fiber device may include a single, cantilevered optical fiber that may be vibrated and scanned in one or two dimensions in a scan pattern to construct an image.

Constructing an image may include acquiring an image of a target area and/or displaying an image on a target area. In acquiring an image-of the target area, the scanning fiber device may scan an illumination spot through an optional lens system and over the target area in the scan pattern. Backscattered light may be captured, for example by a photosensor, in time series. In displaying or forming an image on the target area, the light emitted from the end of the optical fiber may be modulated during the scan pattern depending on the pixel position in order to form a desired image on the target area.

In constructing the image, it is generally desirable to accurately know the position of the optical fiber for each and every point of the scan. Positional inaccuracy may tend to result in distortion of the image constructed. Knowing the drive signal that is used to scan the optical fiber may allow the position of the illumination spot to be estimated for each pixel point during the scan pattern.

In practice however, environmental variables, manufacturing variables, the sensitivity of the scanning fiber device around the resonance frequency, and/or other factors, may tend to limit the accuracy of such estimates. If desired, calibration and remapping as described in U.S. Pat. App. Pub. No. 20060138238 (Johnston et al.) may be performed to help reduce image distortion due to certain of such factors.

However, this calibration and remapping approach is not perfect for environmental variables that may change rapidly during use and/or assume many different values. Consequently, there may be advantages to methods, apparatus, systems, and kits, which may help to reduce image distortion due to environmental variables in an image created or acquired by a scanning beam device, such as, for example, a scanning fiber device.

BRIEF DESCRIPTION OF THE SEVERAL VIEWS OF THE DRAWINGS

The invention may best be understood by referring to the following description and accompanying drawings that are used to illustrate embodiments of the invention. In the drawings.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

Temperature is one environmental variable that may affect the operation of a scanning beam device. Temperature variation, if unaccounted for, may tend to add to the positional inaccuracy of a scanning optical element of the device. Without limitation, this may be, due at least in part, to the affect of temperature variation on properties of materials associated with the movement of the scanning optical element. Such positional inaccuracy may tend to add distortion to the image constructed using the scanning beam device and is generally undesirable.

Figure 1:
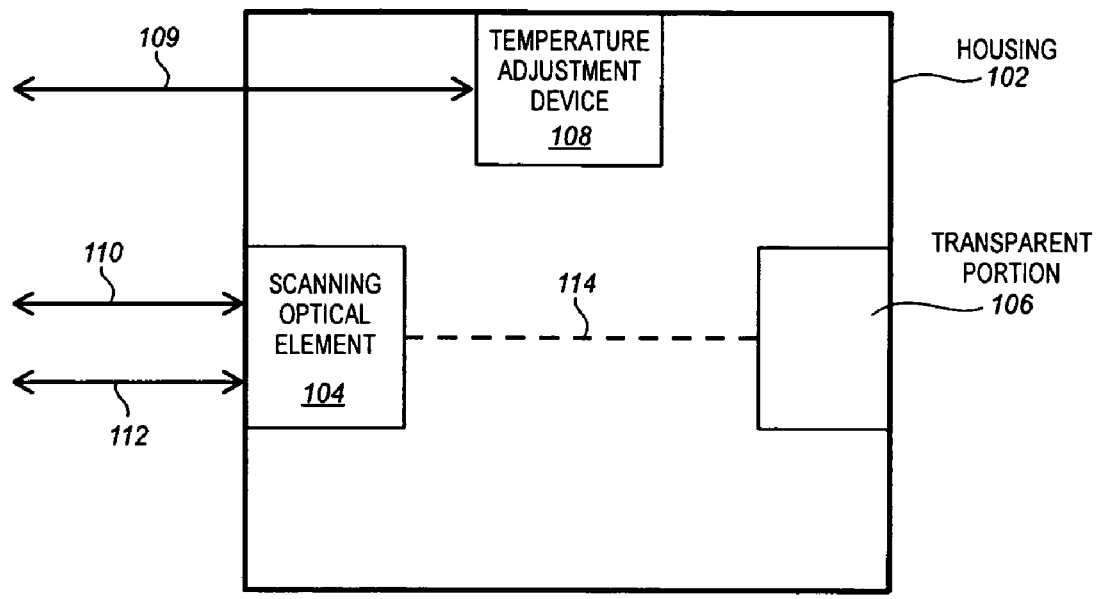
FIG. 1 is a block diagram of an example scanning beam device having a temperature adjustment device, according to an embodiment of the invention.

FIG. 1 is a block diagram of an example scanning beam device 100 having a temperature adjustment device 108, according to an embodiment of the invention. In various embodiments of the invention, the scanning beam device may take the form of an endoscope, scanning fiber endoscope, catheter, bronchoscope, fiberscope, microscope, boroscope, bar code reader, image display, scanning fiber display, or other image acquisition and/or display device known in the art.

The scanning beam device includes a housing 102. The housing may represent a material or device of enclosure. The scope of the invention is not particularly limited to the size and shape of the housing, as this may vary considerably depending upon the particular form assumed by the scanning beam device. In some implementations, such as, for example, in the case of an endoscope, catheter, or like device, the housing may be relatively small, for example to facilitate insertion of the device into a patient. However there may be no such need in other implementations. In some implementations, such as, for example, in the case of an device to be inserted into a patient, the housing may be hermetically sealed, although this is not required in other implementations.

The housing has a transparent portion 106. The transparent portion is transparent to at least some light directed through it, in either or both directions. In one or more embodiments of the invention, the transparent portion may optionally include one or more lenses (for example a lens system), although this is not required. As another option, in one or more embodiments of the invention, the transparent portion may optionally include a simple window or other transparent material other than a lens. The transparent portion may be located or positioned in an optical path of light directed to and/or from a scanning optical element 104. As shown in the illustrated embodiment, the transparent portion may optionally be located at, or towards, an end of the device. Alternatively, the transparent portion may be located on a side of the housing, or elsewhere.

The scanning optical element 104 is enclosed within the housing. For clarity, the term "scanning" in "scanning beam device", "scanning optical element", and like devices or apparatuses, does not necessarily imply that the device or apparatus is in use, or presently in the process of scanning. Rather, the term "scanning" merely implies that the device or apparatus is capable of scanning.

The scanning optical element may include an optical element, such as for example, a waveguide, mirror, or lens, which may be scanned or otherwise moved for purposes of image acquisition and/or display. The scanning optical element may receive light or optical signals 110, and electrical signals 112 to control the movement of the optical element. The scanning optical element may scan or move a beam of light over different portions of a target surface and/or acquire light from different portions of the target surface. The light may have the form of a beam of light, although there is no requirement that the beam be collimated or have parallel rays of light, although it may. As shown, light 114 maybe directed, in either or both directions, between the scanning optical element and the transparent portion of the housing.

Accordingly, the scanning optical element may move. As previously mentioned, temperature may potentially affect properties of materials associated with the movement of the scanning optical element. Changes in these properties may affect how the scanning optical element moves for a given drive signal or actuation. This may tend to hamper the accuracy of the estimates of the position of the scanning optical element, which may lead to distortion-of the image constructed using the scanning beam device.

To further illustrate, it may be helpful to consider several exemplary different types of suitable scanning optical elements, and the various ways in which their operation and/or image quality may potentially be affected by temperature.

Figure 2A:
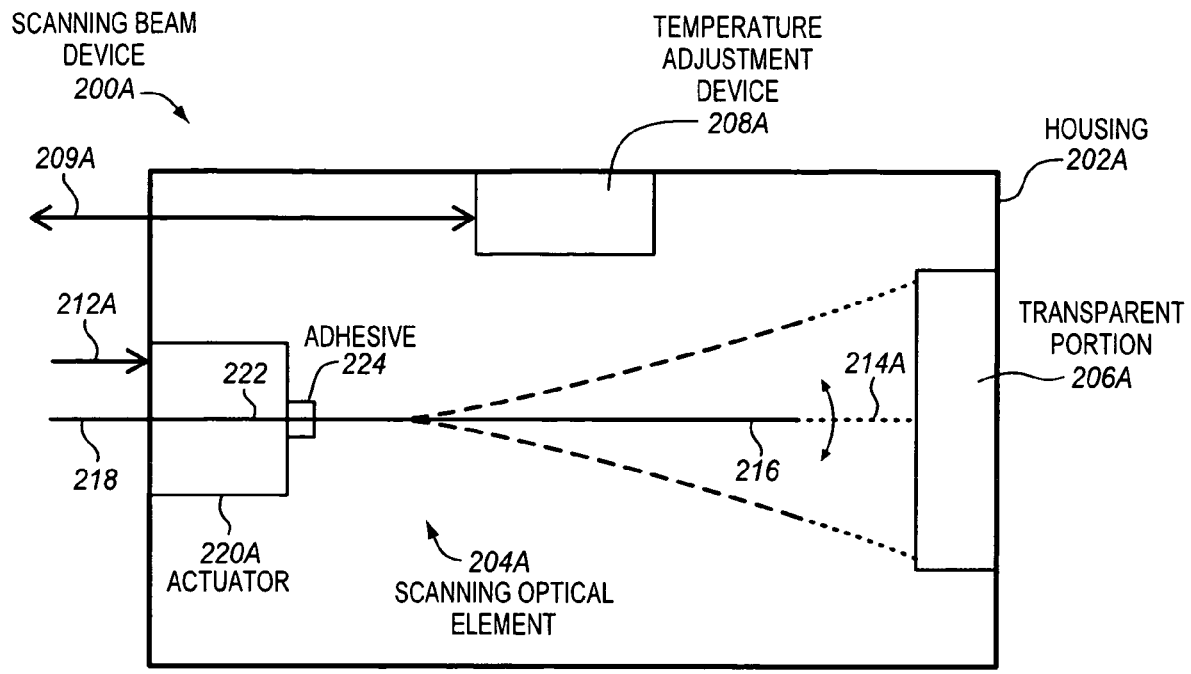
FIG. 2A is a block diagram of first example scanning beam device, according to one or more embodiments of the invention.

FIG. 2A is a block diagram of first example scanning beam device 200A, according to one or more embodiments of the invention. The scanning beam device includes a first type of scanning optical element 204A. In particular, the scanning optical element includes a single, cantilevered, free end portion 216 or distal tip of an optical fiber, Micro-Electro-Mechanical System (MEMS) optical waveguides, micromachined optical waveguide, or other optical waveguide 218 enclosed within a housing 202A, and an actuator 220A configured to move the free end portion.

The optical waveguide has a restrained portion 222. As shown, in one or more embodiments, the actuator may be coupled with the restrained portion, although this is not required. In one or more embodiments of the invention, an adhesive 224 may optionally be used to restrain, adhere, or couple the restrained portion with the actuator or another anchor, although this is not required.

In the description and claims, the terms "coupled" and "connected," along with their derivatives, are used. These terms are not intended as synonyms for each other. Rather, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other physically, electrically, or optically. For example, the restrained portion of the optical waveguide may be coupled with the actuator through the intervening adhesive even if there is not direct contact between the optical waveguide and the actuator.

The actuator may include a transducer or other material or device to move the free end portion in response to input signals 212A, such as, for example, electrical control signals. In one or more embodiments of the invention, the actuator may include a piezoelectric tube through which the restrained portion is inserted, although the scope of the invention is not so limited. Other suitable actuators include, but are not limited to, other electromechanical transducers, Micro-Electro-Mechanical System (MEMS), electromagnetic materials or devices, electrostatic transducers, electroacoustic transducers, Electroactive Polymer (EAP) materials, and other actuators known in the arts. The scope of the invention is not limited to any known type of actuator.

The free end portion of the optical waveguide is free to resonate or otherwise move, in at least one dimension, as a result of the actuator. An arrow is used to show how the free end portion may move. Dashed lines are used to show possible alternate positions of the free end portion of the optical waveguide as a result of movement. In one aspect, the optical waveguide may resonate or otherwise move according to a scan pattern in order to provide light 214A to, and/or acquire light 214A from, different regions of a transparent portion 206A of the housing. Suitable scan patterns include, but are not limited to, radial scan patterns, such as ovals, circles, spirals, propeller patterns, and combinations thereof, and non-radial scan patters, such as raster scan patterns, Lissajous scan patterns, and combinations thereof. The scan patterns may be one-dimensional or two-dimensional.

The free end portion of the optical waveguide may potentially have one or more mechanical properties, such as, for example, elasticity and/or flexibility, which may change with temperature. Likewise, the adhesive (if present) may potentially have one or more mechanical properties, such as, for example, elasticity and/or hardness, which may change with temperature. Certain actuation mechanisms may also potentially change with temperature. Such changes may tend to affect how the optical waveguide moves for a given drive signal and/or amount of applied force. At resonance, the movement of the free end portion of the optical waveguide may be relatively sensitive to such changes. This, if unaccounted for, may tend to promote positional inaccuracy, which may tend to result in increased image distortion.

Figure 2B:
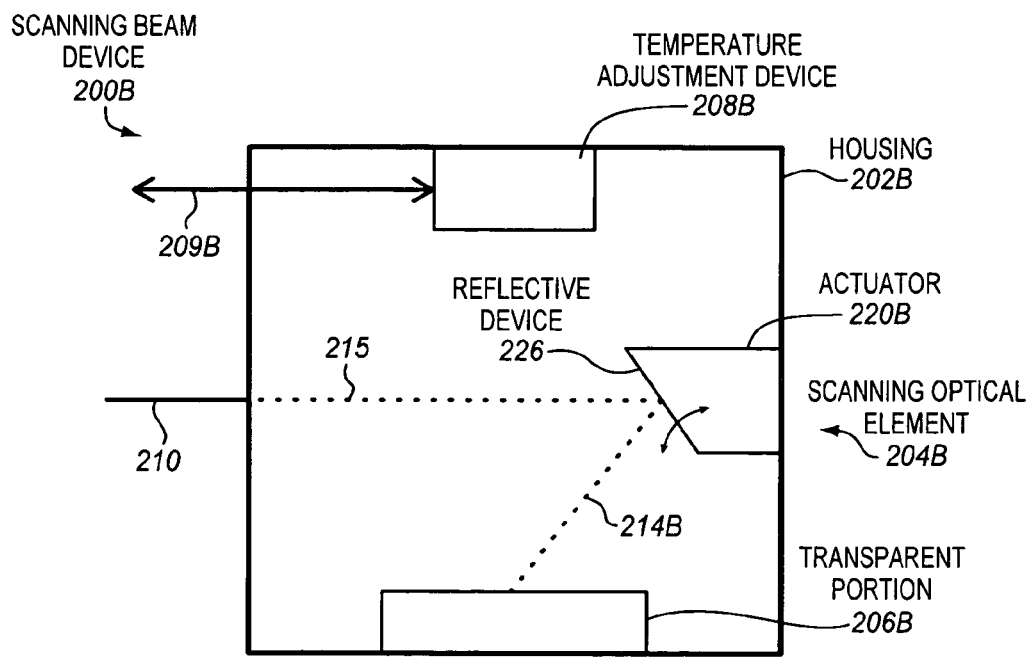
FIG. 2B is a block diagram of a second example scanning beam device, according to one or more embodiments of the invention.

FIG. 2B is a block diagram of a second example scanning beam device 200B, :according to one or more embodiments of the invention. The scanning beam device includes a second type of scanning optical element 204B. In particular, the scanning optical element includes a mirror or other reflective device 226, and a Micro-Electro-Mechanical System (MEMS) or other actuator 220B to move the reflective device.

The housing has a transparent portion 206B. As shown, the transparent portion may be located on a side of the housing, or elsewhere. First light 214B may be directed between the reflective device and the transparent portion in either or both directions. Likewise, second light 215 may be directed between the reflective device and a waveguide or other transparent medium 210 outside of the housing in either or both directions.

The actuator may potentially have one or more mechanical properties, such as, for example, elasticity and/or flexibility, which may change with temperature. Such changes may tend to affect how the reflective device moves. This, if unaccounted for, may tend to promote positional inaccuracy during the scan, which may tend to result in increased image distortion.

Other scanning optical elements are contemplated. For example, another scanning optical element may include a lens or other focusing device that may be moved by a MEMS or other actuator. As other examples, the scanning optical element may include a galvanometer, multiple optical elements moved relative to each other, and the like, and combinations thereof. Still other suitable scanning optical elements are known in the arts and/or will be apparent to those skilled in the art and having the benefit of the present disclosure. In a wide variety of such different types of scanning optical elements, one or more properties of one or more materials associated with the movement of the scanning optical element may potentially change with temperature.

Referring again to FIG. 1, the scanning beam device includes a temperature adjustment device 108. The temperature adjustment device may receive electrical signals 109 from another component, such as, for example, a controller, which may specify or control their operation. Similarly, the scanning beam devices in FIGS. 2A-B include temperature adjustment devices 208A, 208B to receive electrical signals 209A, 209B.

The temperature adjustment devices may adjust temperatures within the respective housings or otherwise adjust temperatures of the respective scanning optical elements based on the electrical signals. In one or more embodiments of the invention, this adjustment of the temperature may be used to regulate or maintain a substantially constant temperature within the housing to reduce positional inaccuracy and/or image distortion, although the scope of the invention is not limited in this respect. For example, in various other embodiments of the invention, the temperature adjustment may be performed to achieve heating (for example to allow use in a cold environment), cooling (for example to allow use in a hot environment), or defogging, whether or not positional inaccuracy and/or image distortion are reduced.

Different types of temperature adjustment devices will now be discussed.

In one or more embodiments of the invention, the temperature adjustment device may include a heater. The heater may increase the temperature within the housing, or otherwise increase the temperature of the scanning optical element, by generating heat. One type of heater that may be used is an electrical resistance heater, although the scope of the invention is not so limited. The electrical resistance heater may convert electrical energy into heat through electrical resistance. Examples of suitable electrical resistance heaters include, but are not limited to, coil resistance heaters, thin film resistance heaters, cartridge resistance heaters, positive temperature coefficient (PCT) resistance heaters, other resistance heaters known in the arts, and combinations thereof. Examples of suitable coil resistance heaters include, but are not limited to, resistive metal coil resistance heaters, wire coil resistance heaters, wound thin film coil resistance heaters, wound tape coil resistance heaters, other coil resistance heaters known in the arts, and combinations thereof. Alternatively, other types of heaters known in the arts may optionally be used.

Figure 3A:
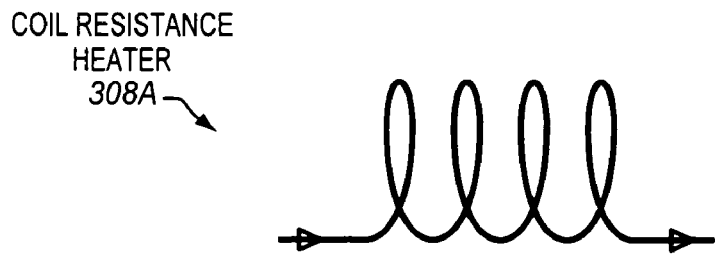
FIG. 3A is a perspective view of a coil resistance heater, according to one or more embodiments of the invention.

FIG. 3A is a perspective view of a coil resistance heater 308A, according to one or more embodiments of the invention. The coil resistance heater includes a number of windings or other loops, in a generally helical form. The illustrated heater includes about four loops, although alternate heaters may optionally include fewer or more loops, even many more loops. In one or more embodiments of the invention, the coil resistance heater may be formed by winding a resistive wire or other resistive material about a cylinder, although this is not required. Suitable resistive wire includes, but is not limited to, nickel-chromium resistance wires of various different alloys and compositions.

During operation, temperatures at ends of such a coil resistance heater may tend to be slightly lower than temperatures at the center. The loops at the ends may have greater access to volumes of cooler air, such as the air at the ends of the coil, than the loops at the center. This may result in larger temperature gradients for the loops at the ends, which may result in more rapid heat transfer away from the loops at the ends. This may lead to slightly cooler temperatures at the ends of the coil than towards the center of the coil. In some cases, such cooler temperatures at the ends may be undesirable. For example, in the particular case of a scanning fiber device having a length of optical fiber inside a length of the coil, this may result in different temperatures along the length of the optical fiber, which may tend to affect the movement of the optical fiber in a rather complicated way. Accordingly, in some cases, it may be desirable to eliminate, or at least reduce, the temperature difference between the ends and center of the coil resistance heater.

Figure 3B:
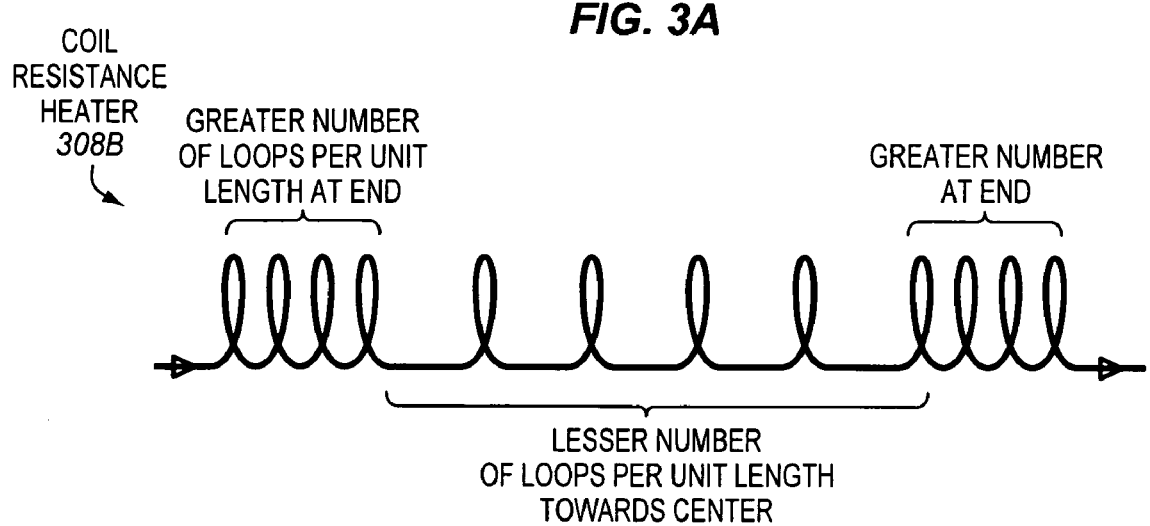
FIG. 3B is a perspective view of a coil resistance heater having a greater number of windings or other loops per unit length at or towards the ends than at or towards a center, according to one or more embodiments of the invention.

FIG. 3B is a perspective view of a coil resistance heater 308B having a greater number of windings or other loops per unit length at or towards the ends than at or towards a center, according to one or more embodiments of the invention. In the illustrated embodiment, the spacing between the loops at the end regions is reduced compared to the spacing between the loops at the center region. However, there are other ways of increasing the relative number of windings or other loops per unit length. For example, windings or loops may be wound or stacked over one another. This may work well in the case of a tightly wound coil. The increased number of windings or loops per unit length at or towards the ends compared to at or towards the center may help to increase the temperature at or towards the ends relative to the temperature at or towards the center. In one aspect, the relative number of loops per unit length towards the ends and center may be selected to provide substantially uniform temperatures along a length of the heater, although this is not required. For example, the temperature variation along the coil resistance heater may vary by less than about 2° C., or another value suitable for the implementation.

Electrical current flowing through coil resistance heaters may generate magnetic fields. Such magnetic fields may, at times, be undesirable. For example, such magnetic fields may be undesirable when the scanning beam device is used for magnetic resonance imaging (MRI), magnetic resonance tomography (MRT), nuclear magnetic resonance (NMR), or the like. In certain instances, such magnetic fields may be undesirable if they interfere with the operation of other circuits or devices in the vicinity. Accordingly, in some cases, it may be desirable to eliminate, or at least reduce, the magnetic fields generated by coil resistance heaters.

Figure 3C:
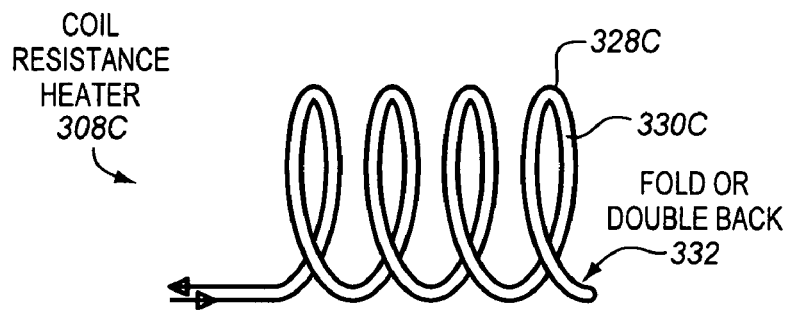
FIG. 3C is a perspective view of an example coil resistance heater having adjacent loops or coils coupled to flow current in opposite directions using a first approach, according to one or more first embodiments of the invention.

FIG. 3C is a perspective view of an example coil resistance heater 308C having adjacent loops or coils 328C, 330C coupled to flow current in opposite directions using a first approach, according to one or more first embodiments of the invention. The coil resistance heater includes a bifilar coil. The bifilar coil may include two adjacent, closely spaced, parallel coils 328C, 330C having a number of corresponding adjacent, closely spaced, parallel loops. By way of example, the bifilar coil may be formed from a wire or other resistive material that has been folded or otherwise doubled back on itself, and then wound or otherwise formed into the bifilar coil. A fold or "double back" 332 is illustrated at the end of the bifilar coil on the right-hand side. The adjacent loops or coils may be electrically coupled to flow current in opposite directions. In particular, one of the ends of the wire at the left-hand side may be coupled with a current source and another of the ends of the wire may be coupled with a current sink. Current may flow from the current source, through a first coil of the bifilar coil in a first direction to the fold or double back, and then flow back through a second coil of the bifilar coil in a second, opposite direction to the current sink. Arrows show that current may flow in opposite directions through the adjacent loops or coils of the bifilar coil. As shown, both ends of the wire are located at the same side of the heater (the left-hand side in the illustrated embodiment). Having both ends of the wire at the same end may facilitate making electrical connections to the ends, especially when the heater is small and is deployed in a small housing.

In some cases, such as for small diameter wires and/or insufficiently ductile materials, the fold or double back may be susceptible to breakage. In one or more embodiments of the invention, two separate wires may each be wound into a coil, and then the ends of the wires located on the same side of the heater may be soldered or otherwise electrically coupled or joined to form the equivalent of a fold or double back. This may help to reduce breakage. Furthermore, if breakage occurs when a wire is folded or wound as described previously, the broken ends may be soldered or otherwise rejoined.

Figure 3D:
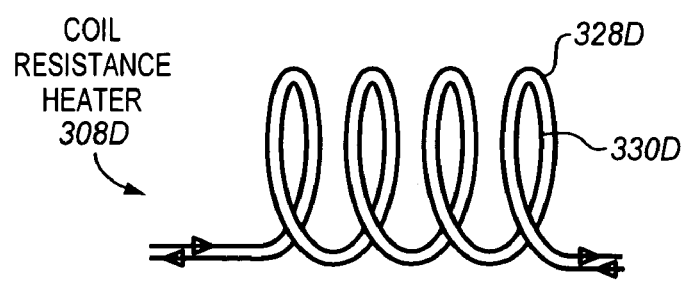
FIG. 3D is a perspective view of a coil resistance heater having adjacent loops or coils coupled to flow current in opposite directions using a second approach, according to one or more second embodiments of the invention.

FIG. 3D is a perspective view of a coil resistance heater 308D having adjacent loops or coils 328D, 330D coupled to flow current in opposite directions using a second approach, according to one or more second embodiments of the invention. As before, the coil resistance heater includes a bifilar coil including two adjacent, closely spaced, parallel coils 328C, 330C having a number of corresponding adjacent, closely spaced, parallel loops. However, in this bifilar coil, the coils are not electrically connected with one another. That is, there is no fold or double back. Rather, two separate strands of wire or other resistive material are wound or otherwise formed into the bifilar coil. Again, the adjacent loops or coils may be electrically coupled to flow current in opposite directions. In particular, a left-hand end of a first coil -may be electrically coupled with a current source, and a right-hand end of the first coil may be electrically coupled with a current sink. Continuing, a right-hand end of a second coil may be electrically coupled with a current source, and a left-hand end of the second coil may be electrically coupled with a current sink. Arrows show that current may flow in opposite directions through the adjacent loops or coils of the bifilar coil.

Yet another contemplated way of having adjacent loops or coils coupled to flow current in opposite directions includes winding or otherwise forming two layers of wire or other resistive material, with each layer wound in a different direction, optionally with approximately equal numbers of turns. These are just a few illustrative examples.

In such electrical resistance coils, the magnetic field created by the flow of current in the loops of one coil in one direction may be about equal and opposite to the magnetic field created by the flow of current in the opposite direction in the loops of the other coil. Such about equal and opposite magnetic fields may tend to negate or cancel. If the number of adjacent, corresponding loops are about equal in each direction, as in the illustrated heaters, this may result in a net magnetic field of about zero. In other words, the bifilar coil may have a self-inductance of about zero. Such an approach may be used to reduce magnetic fields when the scanning beam device is used for magnetic resonance imaging (MRI), magnetic resonance tomography (MRT), nuclear magnetic resonance (NMR), or the like, or when magnetic fields are otherwise undesirable.

Figure 3E:
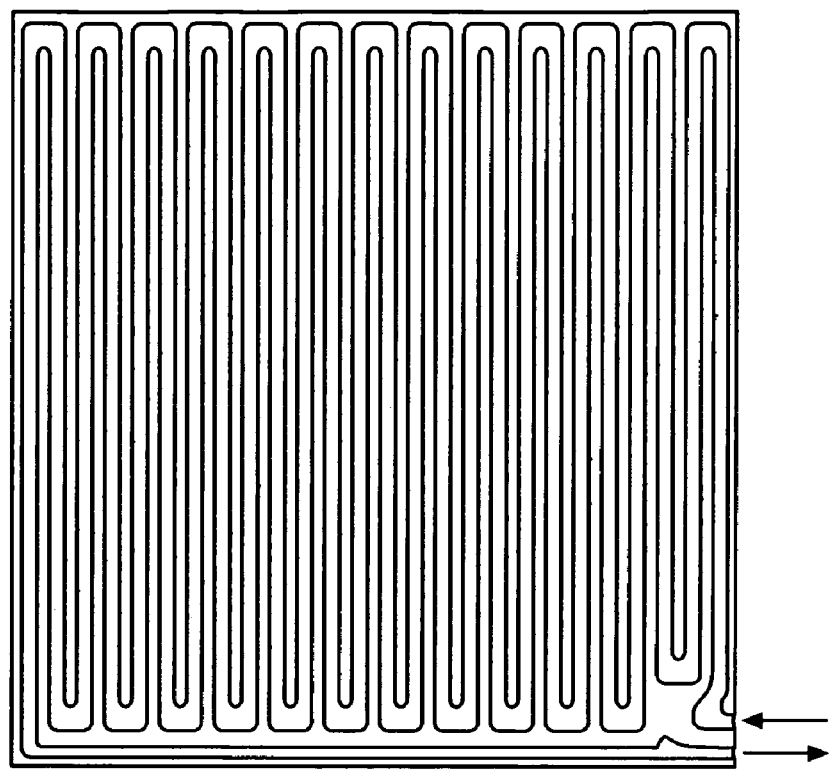
FIG. 3E is a top planar view of a thin-film resistance heater, according to one or more embodiments of the invention.

FIG. 3E is a top, planar view of a thin-film resistance heater 308E, according to one or more embodiments of the invention. The thin film resistance heater includes a number of generally coplanar, serpentine windings of a patterned resistive layer formed over a substrate. Such a heater may optionally be made quite small. By way of example, in one particular embodiment of the invention, the heater may be fabricated of platinum, be about 270 micrometers ($\mu$m) by 270 $\mu$m, have platinum lines about 5 $\mu$m wide, and have spacing between the lines of about 5 $\mu$m. The heater may also have other shapes and sizes. For example, the heater may be elongated in either direction by including more serpentine windings or wider windings. In one aspect it may be elongated along a length of a free end portion of an optical fiber. If desired, an array or other plurality of such heaters may be used to provide additional heating. In one aspect, the array may be provided along a length of a free end portion of an optical fiber. In one or more embodiments of the invention, a thin-film resistance heater or array or other plurality of thin-film resistance heaters may be formed on a flexible substrate or support, and may be wrapped or otherwise formed into a cylinder or other non-planar shape.

Figure 3F:
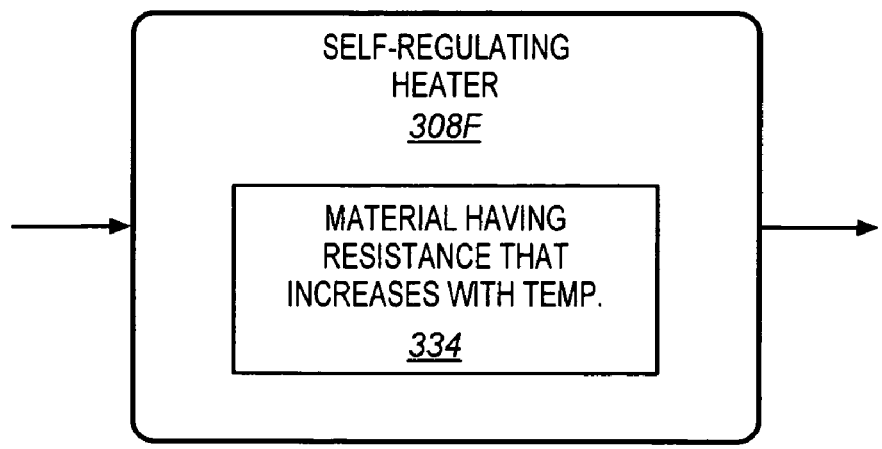
FIG. 3F is a block diagram of a self-regulating resistive heater, according to one or more embodiments of the invention.

FIG. 3F is a block diagram of a self-regulating resistive heater 308F, according to one or more embodiments of the invention. The self-regulating resistive, heater includes a material having a resistance that increases with increasing temperature 334.

One type of material having a resistance that increases with increasing temperature is a positive coefficient of temperature (PCT) material. Example PCT materials are described in U.S. Pat. No. 5,212,466, entitled "PTC THERMISTOR AND MANUFACTURING METHOD FOR THE SAME". Other example PCT materials are described in patent reference WO/2003/019578, entitled "CONDUCTIVE POLYMER HAVING POSITIVE TEMPERATURE COEFFICIENT, METHOD OF CONTROLLING POSITIVE TEMPERATURE COEFFICIENT PROPERTY OF THE SAME AND ELECTRICAL DEVICE USING THE SAME". Still other example PCT materials are described in patent reference WO/2002/047093, entitled "POSITIVE TEMPERATURE COEFFICIENT THERMISTOR". Other examples of PCT materials are known in the arts.

For a given voltage (V) applied across a resistive heater, the current (I) flowing through the resistive heater and the resistance (R) of the resistive heater are inversely related according to the equation V=IR. The power (P) converted into heat by a resistive heater is approximately equal to the current (I) squared, multiplied by the resistance (R) according to the equation $P=I^2R$. Accordingly, for a given voltage (V) across the resistor, if the resistance (R) increases, due to increasing temperature, then the current (I) will decrease. Since the current (I) has a second order (squared) effect on the heat generated, and since the resistance (R) only has a first order effect on the heat generated, a decrease in the current (I) will decrease the heat generated. Accordingly, at lower temperatures the resistive heater will generate more heat, while at higher temperatures the resistive heater will generate less heat.

This self-regulating characteristic of the heater may be used to regulate or control the temperature of the scanning optical element toward a substantially constant value. In one or more embodiments of the invention, such a self-regulating heater may be used in place of a dedicated temperature sensor and feedback control mechanism. Furthermore, if desired, the current flowing through such a material may be measured, the measured current may be used to estimate the resistance, the resistance may be used to estimate the temperature, and the temperature may be used for purposes of temperature regulation or control. Alternatively, as described further below, a dedicated temperature sensor device and feedback control mechanism may optionally be used.

Several different types of heaters have been shown and described, although the scope of the invention is not limited to these particular heaters. Many further examples of heaters are contemplated. For example, a bifilar coil, such as those shown in FIGS. 3C-D, may optionally have a greater number of windings or other loops per unit length at or towards one or more ends than at or towards a center, for example as shown in FIG. 3B. As another example, a PCT or other material having a resistance that increases with temperature may be used in a coil, bifilar coil, or thin-film resistive heater. Many further examples of heaters will be apparent to those skilled in the art and having the benefit of the present disclosure.

As yet another option, in one or more embodiments of the invention, the temperature adjustment device may include a cooler. The cooler may decrease the temperature within the housing, or otherwise decrease the temperature of the scanning optical element by removing heat. Examples of suitable coolers include, but are not limited to, Peltier devices, other thermoelectric cooling devices known in the arts, and heat pipes. Alternatively, other coolers known in the arts may optionally be used.

The temperature adjustment devices shown and described herein may have various different sizes and shapes depending upon the particular form assumed by the scanning beam device. In some implementations, such as, for example, in the case of an endoscope, catheter, or like device to be inserted into a patient, the heaters may be relatively small. However there may be no such need in other implementations. For example, in the case of a display device, there may be no need for such a small size.

Figure 4:
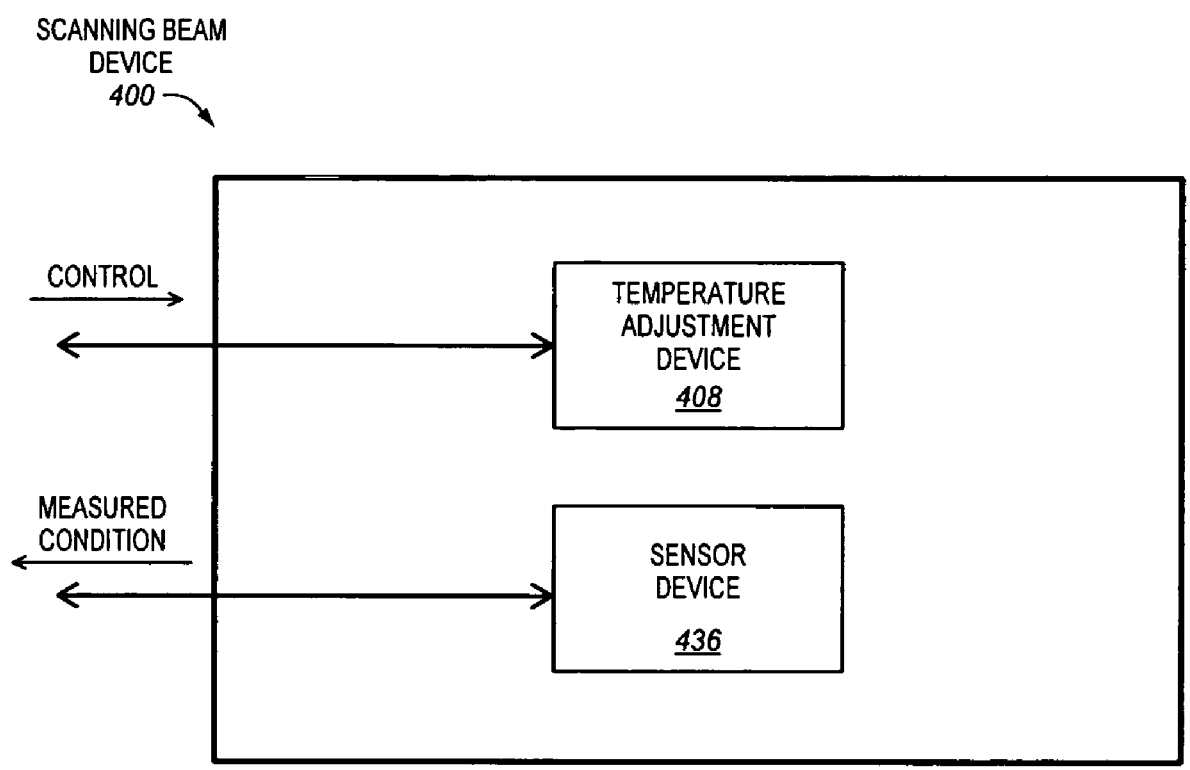
FIG. 4 is a block diagram of a scanning beam device having a temperature adjustment device and a sensor device, according to one or more embodiments of the invention.

FIG. 4 is a block diagram of a scanning beam device 400 having a temperature adjustment device 408 and a sensor device 436, according to one or more embodiments of the invention. The sensor device may be enclosed within a housing of the scanning beam device. The sensor device may sense or measure a condition within the housing, or otherwise sense or measure a condition of the scanning beam device. In one or more embodiments of the invention, the temperature adjustment device may be controlled based on the sensed condition to maintain a constant temperature within the housing.

In one or more embodiments of the invention, the sensor device may include a temperature sensor device to sense or measure a temperature. Examples of suitable temperature sensor devices include, but are not limited to, thermocouples, resistive temperature devices (RTDs), and thermistors.

Alternatively, in one or more embodiments of the invention, the sensor device may include a pressure sensor device to sense or measure a pressure. In a sealed, constant-volume housing, the temperature is approximately directly proportional to the pressure within the housing. Under such circumstances, pressure may be sensed or measured and used to estimate a corresponding temperature according to a fixed proportionality constant. Examples of suitable pressure sensors include, but are not limited to, MEMS pressure sensors, piezoelectric pressure sensors, other types of pressure sensors known in the arts, and combinations thereof.

Each of the sensor device and the temperature adjustment device may be electrically coupled with or otherwise in communication with another component (not shown), such as a controller. The sensor device may provide the sensed condition to the other component. The other component may use the sensed condition to control the temperature adjustment device.

Figure 5:
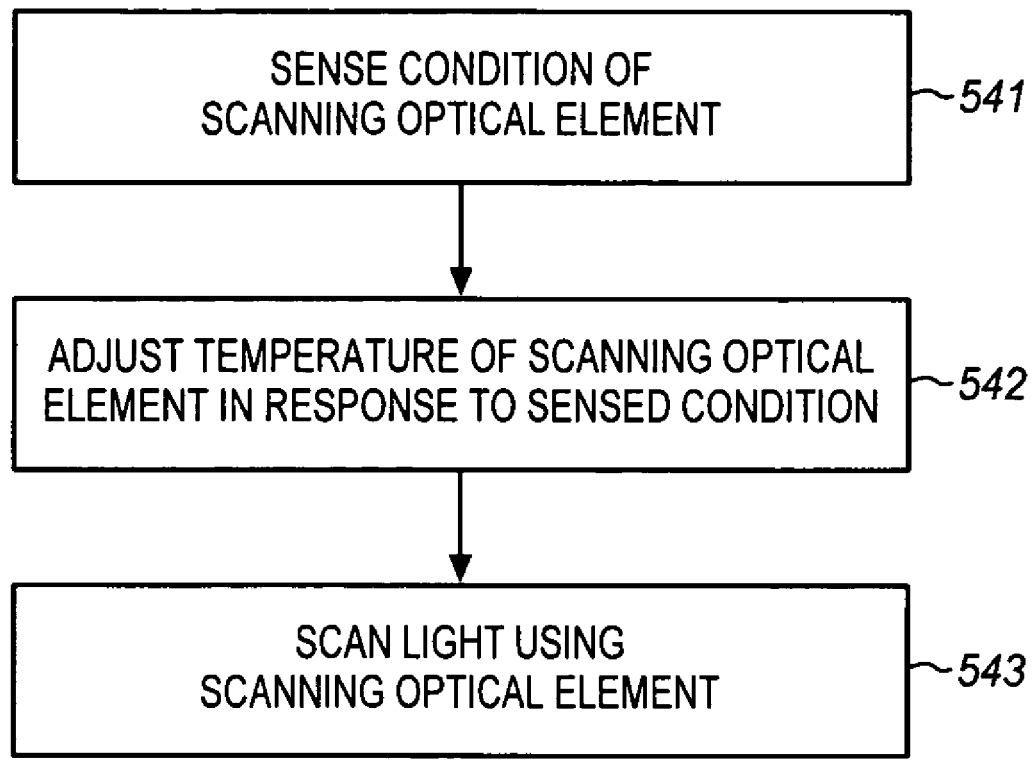
FIG. 5 is a block flow diagram of a method performed by a scanning beam device, according to one or more embodiments of the invention.

FIG. 5 is a block flow diagram of a method 540 performed by a scanning beam device, according to one or more embodiments of the invention.

The method includes sensing a condition of a scanning optical element, at block 541. In one or more embodiments of the invention, this may include sensing a temperature of the scanning optical element, for example sensing an ambient temperature around the scanning optical element. As another option, in one or more embodiments of the invention, this may include sensing a pressure of a sealed, constant volume housing enclosing the scanning optical element.

The method further includes adjusting a temperature of the scanning optical element in response to the sensed condition, at block 542. In one or more embodiments of the invention, this may include increasing the temperature of the scanning optical element by heating. As another option, in one or more embodiments of the invention, the temperature of the scanning optical element may be decreased by cooling. The amount to adjust the temperature may, in one or more embodiments of the invention, be determined by using an algorithm. For example, in one or more embodiments of the invention, the amount of temperature adjustment may be determined to maintain the temperature of the scanning optical element at a substantially constant value. As discussed elsewhere herein, this may help to reduce distortion in an image constructed using the scanning optical element.

In one or more embodiments of the invention, adjusting the temperature may include increasing the temperature of the transparent material to value that is not less than a temperature of a humid or moist environment in which the scanning optical element is deployed to reduce fogging or moisture accumulation on a transparent material in an optical path of light directed through the scanning optical element. For example, in the case of an endoscope or like device deployed in a patient, the transparent material may be heated to a temperature ranging from about body temperature (37° C.) to about 10° C. higher than body temperature, although the scope of the invention is not so limited.

The method further includes scanning light using the scanning optical element, at block 543. In one or more embodiments of the invention, this may include resonating or otherwise moving a single, cantilevered optical fiber or other optical waveguide. As another option, in one or more embodiments of the invention, this may include moving a mirror, lens, or other optical element. If the scanning optical element is controlled to have a substantially constant temperature, distortion of images displayed or acquired using the scanning optical element may be advantageously reduced.

Many variations on the above-described method are contemplated. In one aspect, operations may be added to and/or removed from the methods. For example, the operation of sensing may optionally be omitted. In another aspect, the operations may optionally be performed in different order. For example, scanning may begin before sensing and/or adjustment. As another example, temperature adjustment may begin before conditions are sensed.

Figure 6:
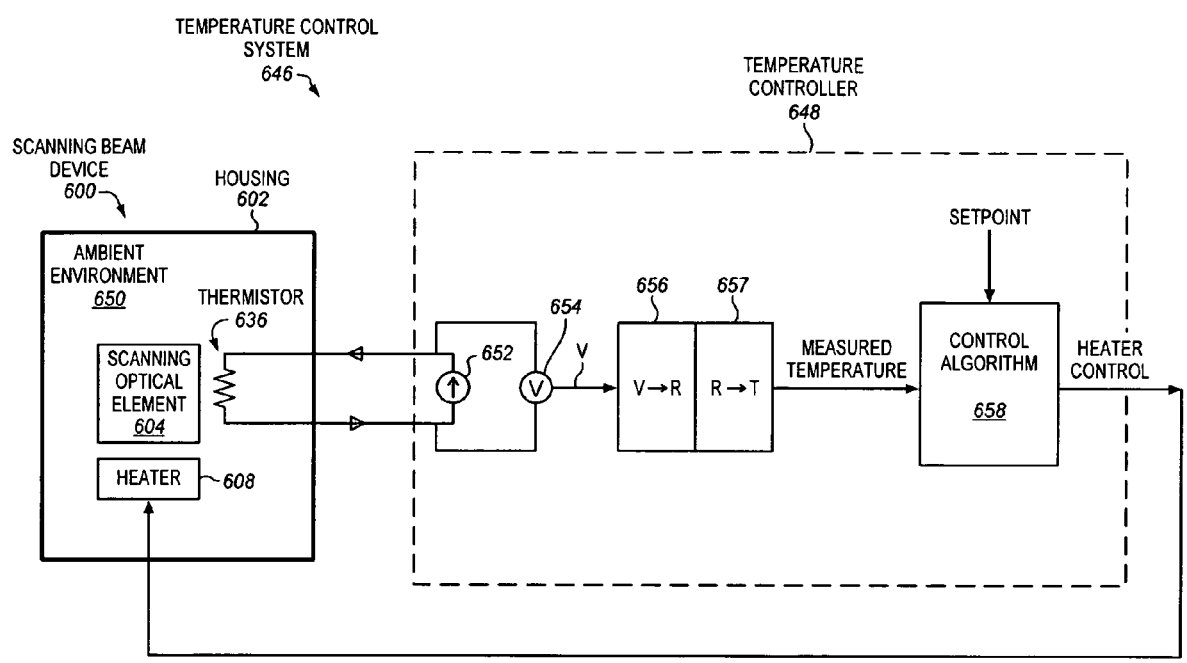
FIG. 6 is a block diagram of a temperature control system, according to one or more embodiments of the invention.

FIG. 6 is a block diagram of a temperature control system 646, according to one or more embodiments of the invention. The temperature control system includes a scanning beam device 600 and a temperature controller 648.

The scanning beam device has a scanning optical element 604, enclosed within a housing 602, in an ambient environment 650. The scanning beam device includes a thermistor 636, representing one possible type of sensor, and a heater 608, representing one possible type of temperature adjustment device. Both the thermistor and the heater are enclosed within the housing, in the ambient environment, proximate the scanning optical element.

The temperature controller is electrically coupled with the scanning beam device. In particular, the temperature controller includes a current source 652 coupled to provide current to the thermistor. The amount of current is generally sufficiently small to avoid significant self-heating by the thermistor. The current may either be constant or variable. A voltage measurement device 654, such as, for example, a voltmeter or voltmeter circuit, is coupled to measure a voltage drop (V) across the thermistor.

The measured voltage drop (V) is provided as input to one or more relations 656, 657. By way of example, as shown in the illustrated embodiment, the voltage drop (V) is provided as input to a voltage-to-resistance relation 656. The voltage-to-resistance relation may convert the voltage drop (V) to a resistance (R), for example, by using the well known relation resistance (R) is equal to voltage (V) divided by current (I). As further shown in the illustrated embodiment, the resistance (R) may be provided as input to a resistance-to-temperature relation 657. For a given thermistor, the resistance may change with changing temperature in a known or predetermined way. By way of example, this relation may be known from the thermistor manufacturer or may be empirically measured. As a result, the temperature of the thermistor may be estimated from the known resistance of the thermistor. If the current to the thermistor is sufficiently constant, a single voltage-to-temperature relation may optionally be used in place of the two separate relations described above. Examples of suitable relations include, but are not limited to, equations, tables, and similar types of relations known in the arts. The tables, equations, or other relations may be implemented in hardware, software, or a combination of both hardware and software.

A control algorithm 658 of the temperature controller may receive the measured temperature corresponding to the measured voltage, as well as a setpoint temperature. The setpoint temperature may represent a desired operating temperature for the scanning optical element. The control algorithm may determine a heater control based, at least in part, on the measured and setpoint temperatures. The heater control may attempt to maintain the temperature sensor at the substantially constant setpoint temperature. The control algorithm may-then apply this heater control to the heater. The heater control may take the form of a particular current, voltage, or current-voltage combination. The control algorithm may be implemented in hardware, software, or a combination of both hardware and software.

The scope of the invention is not limited to any known type of control algorithm. Examples of suitable control algorithms include, but are not limited to, on-off control algorithms, proportional control algorithms, proportional-derivative control algorithms, proportional-integral control algorithms, proportional-integral-derivative (PID) control algorithms, and other control algorithms known in the arts. The use of a relatively sophisticated control algorithm, such as a PID control algorithm, may tend to promote accurate and stable control. However, the use of such relatively sophisticated control algorithms is not required. In fact, control algorithm may optionally be replaced by manual adjustment, although this generally tends to provide inferior temperature control.

In various embodiments of the invention, the temperature may be controlled to be within about 5° C., about 3° C., about 2° C., about 1° C., about 0.1° C., or about 0.01° C., of the setpoint temperature, although the scope of the invention is not limited in this respect. The amount of control may depend upon the particular implementation. By way of example, in the particular case of a scanning optical fiber endoscope, for which accurate image acquisition is desired, the temperature may be controlled to be within about 1° C. of the setpoint temperature, although the scope of the invention is not so limited. In accordance with one or more embodiments of the invention, if the scanning beam device is to be used in a humid or moist environment, the setpoint temperature may optionally be about equal to, or greater than, a temperature of the environment in order to help reduce fogging or moisture accumulation-on a lens or other transparent portion of the device. For example, in the case of an endoscope, or other device to be inserted into a patient, the setpoint temperature may optionally be greater than or equal to a body temperature of the patient, which is taken herein to be 37° C. In various embodiments, the setpoint temperature may be from about 0° C. to 10° C. higher than the body temperature of the patient.

Figure 7:
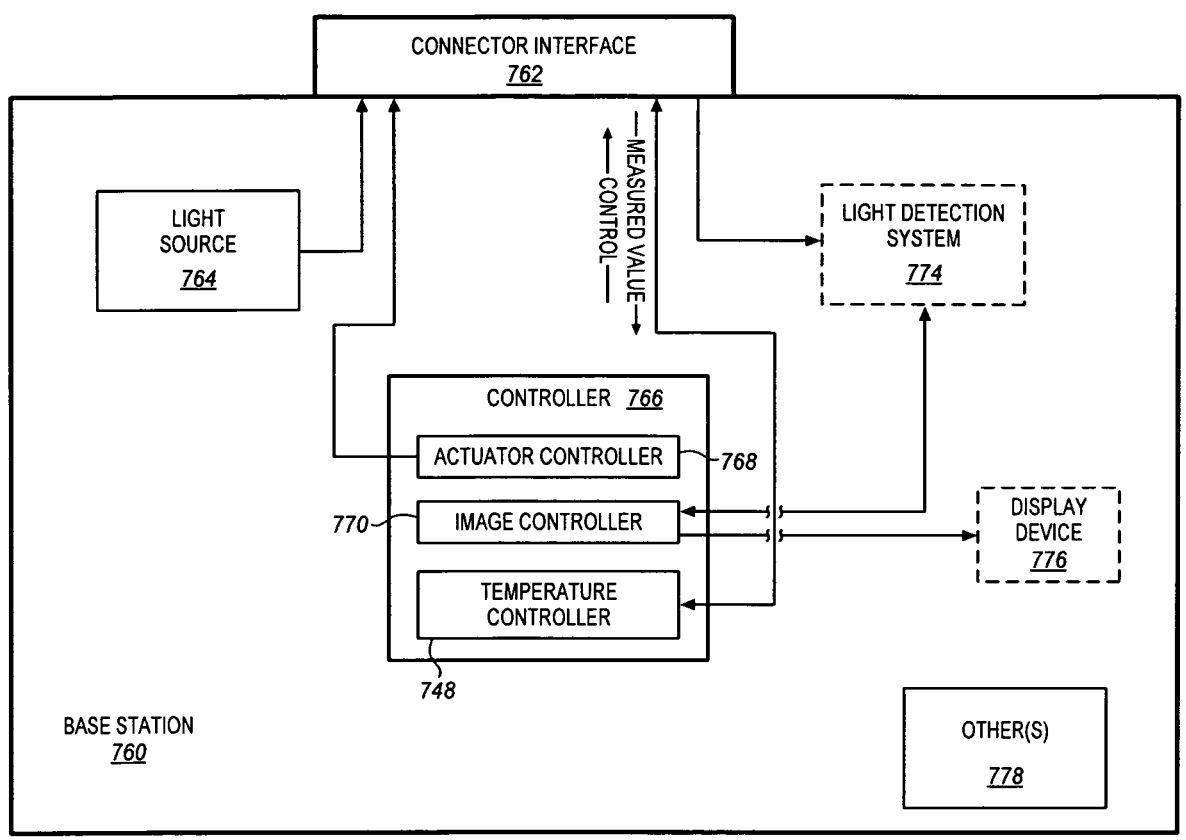
FIG. 7 is a block diagram of a base station for a scanning beam image acquisition device, such as an endoscope, having a scanning optical element, according to one or more embodiments of the invention.

FIG. 7 is a block diagram of a base station 760 for a scanning beam image acquisition device, such as an endoscope, having a scanning optical element, according to one or more embodiments of the invention.

The base station includes a connector interface 762. The connector interface may be used to connect a corresponding connector of a proximal portion of the endoscope or other scanning beam device. Electrical and optical signals may be exchanged between the base station and the endoscope or other scanning beam device through the connector interface.

The base station includes a light source 764. The light source may provide light to the endoscope or other scanning beam device through the interface. In one or more embodiments of the invention, the light source may include multiple different light sources, such as, for example, red, green, and blue light sources, although this is not required.

The base station also includes a controller 766. The controller includes an actuator controller 768. The actuator controller may provide control signals to the endoscope or other scanning beam device through the interface to control movement of the scanning optical element. In one or more embodiments of the invention, the actuator controller may control the scanning optical element to move according to a scan pattern.

In one or more embodiments of the invention, the base station may optionally include a light detection system 774. The optional light detection system may detect light returned from the endoscope or other scanning beam device through the connector interface. In one or more of such embodiments, the optional light detection system may include multiple different light detectors, such as, for example, red, green, and blue light detectors, although this is not required. As another option, the light detection system may optionally be located elsewhere, such as, for example, in the endoscope or other scanning beam device.

Signals representing the detected light may be provided to an image controller 770, either from the light detection system, or from the scanning beam device through the connector interface. The image controller may process the electrical signals to generate images. In one or more embodiments of the invention, the image controller may remap the images using calibration data in order to reduce distortion and/or improve the appearance of the images, although this is not required.

In one or more embodiments of the invention, the base station may optionally include a display device 776. The optional display device may display images to a user. Alternatively, the display device may be separate from the base station and may be capable of being electrically coupled with the base station.

The base station further includes a temperature controller 748. The temperature controller 748 may be the same as or different than the temperature controller 648 shown in FIG. 6. The temperature controller may receive a sensed condition of the scanning optical element through the interface. The temperature controller may determine, and may provide, a responsive control signal to the endoscope or other scanning beam device through the interface to control a temperature of the scanning optical element. In one or more embodiments of the invention, the temperature controller may use an algorithm, such as, for example, a PID algorithm, to determine the control signal. In one or more embodiments of the invention, the temperature controller may regulate or control a temperature of the scanning optical element to have a substantially constant value.

The base station may include other conventional components 778. Examples of other components that may be included in base stations include, but are not limited to, power sources, amplifiers, digital-to-analog converters, analog-to-digital converters, clocks, waveform generators, user interfaces, photosensitive position sensors, calibration chambers, and the like, other components, and various different combinations thereof. To avoid obscuring the description, these components will not be discussed in further detail.

As discussed above, one potential use of heating is to control a temperature of the scanning optical element at a substantially constant value in order to reduce image distortion, although the scope of the invention is not limited in this respect. For example, a heater may be used to heat the device to a temperature equal to or greater than a temperature of a humid environment in which the device is deployed to reduce fogging, whether or not the temperature is controlled to be substantially constant or image distortion is reduced. As another example, a cooler may be used to cool the device to allow the device to be used in a hot environment where its operation or reliability is otherwise hindered. As yet another example, a heater may be used to heat the device to allow the device to be used in a cold environment where its operation may be hindered. Furthermore, even if temperature regulation or control to a substantially constant value is desired, a sensor device is not required. For example, the heater may be self-regulating.

To further illustrate certain concepts, consider a detailed working example of a scanning beam device according to one embodiment of the invention. It is understood that this example are to be construed as merely illustrative, rather than limiting.

Figure 8:
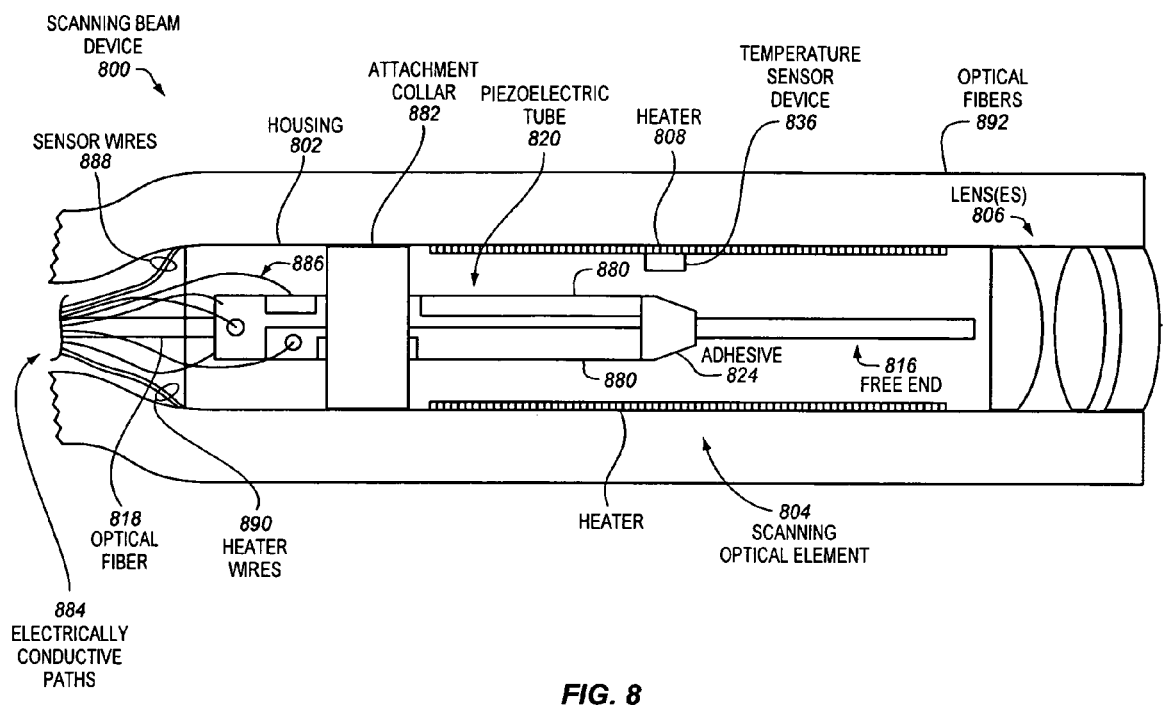
FIG. 8 is a cross-sectional side view of a detailed example of a scanning beam image capture device, according to one or more embodiments of the invention.

FIG. 8 is a cross-sectional side view of a detailed example of a scanning beam image capture device 800, according to one or more embodiments of the invention. The particular illustrated scanning beam device is well suited for use as an endoscope or other instrument or probe for insertion into patients.

The scanning beam device includes a housing 802. The housing may include stainless steel or other materials suitable for deployment in patients. The housing may be sufficiently hermetically sealed for insertion into a patient as an endoscope or like instrument or probe. The housing may be small or minute. For example, in one or more embodiments of the invention, the housing may be generally tubular, have a diameter that is on the order of about 1 to 2 millimeters (mm) or less, and have a length that is on the order of about 10 to 15 mm, or less. However, the scope of the invention is not limited in this respect. Such a minute housing may offer certain advantages when the scanning beam device is to be used as an endoscope or otherwise inserted into a patient, although in other implementations the size and shape of the housing may vary considerably.

A free end portion 816 of an optical fiber 818 is within the housing. A piezoelectric tube 820 is also included within the housing. The piezoelectric tube represents one particular example of an actuator to move the free end portion of the optical fiber. In one or more embodiments of the invention, the piezoelectric tube may include a PZT 5A material, although this is not required. The piezoelectric tube may have an outer diameter of about 0.5 mm. The restrained portion (not shown) of the optical fiber is inserted-through a cylindrical opening in the piezoelectric tube. An adhesive 824 is used to restrain, adhere, or otherwise couple the restrained portion of the optical fiber to the piezoelectric tube. One particular example of a suitable adhesive is Super Glue brand cyanoacrylate, although this adhesive is not required. In one or more embodiments of the invention, the piezoelectric tube may have four, quadrant metal electrodes 880 plated thereon to move the optical fiber in two dimensions. An attachment collar 882 may couple the piezoelectric tube with the housing. The piezoelectric tube may be inserted through a tightly fitting generally cylindrical opening through the attachment collar.

The scanning beam device includes a temperature sensor device 836 to sense a temperature within the housing. Examples of suitable temperature sensor devices include, but are not limited to, thermocouples, resistive temperature devices (RTDs), and thermistors. One particular example of a suitable thermistor includes a multilayer NTC Panasonic series ERTJ size 0201 (about 2 mm×1 mm) thermistor, which is commercially available from Panasonic, of Secaucus, N.J. This thermistor has a resistance of about 10 kΩ. In one or more embodiments of the invention, the thermistor may optionally be grinded or otherwise machined down by approximately half in order to further reduce its size, although this is not required. If done, the resistance may change and the thermistor should be recalibrated.

The scanning beam device includes a heater 808 to increase the temperature within the housing in response to the sensed temperature. The heater may include a coil resistance heater. The coil resistance heater may be formed by winding a small diameter wire into a coil. The wire may optionally be folded or doubled back on itself and wound into a bifilar coil. This may allow both ends of the wire to be on the same side. Additional windings per unit length may optionally be provided at the ends to promote even temperatures across the length of the heater. An example of suitable wire is 36 cm EVANOHM® nickel-chromium resistance wire, available from Wilbur B. Driver Co., which has a resistance of about 400 Ω/ft, although the scope of the invention is not limited to this particular type of wire. As shown, the coil resistance heater may be placed on an inside of the inner wall of the housing. As another option, in one or more embodiments, the coil resistance heater may be placed outside of the housing. As shown, the coil may surround the free end portion of the optical fiber and may span a substantial, length thereof. In one particular embodiment of the invention, the heater includes a bifilar coil of 36 μm EVANOHM® nickel-chromium resistance wire that is folded or doubled back on itself, having about 300 loops, a length of about 6 mm, and a diameter of about 0.9 mm, however this particular heater is not required. Such a heater may be capable of producing around 30 milliwatts of heat on average.

As shown, in one or more embodiments of the invention, the temperature sensor device may be positioned proximate the adhesive. Temperature may affect the properties of the adhesive, and thereby affect the movement of the free end portion of the optical fiber. Placing the thermistor or other temperature sensor device proximate the adhesive may promote accurate measurement of the temperature of the adhesive. By way of example, for such a small device to be inserted into a patient, the thermistor may be within about 5 mm of the adhesive. As further shown, in one or more embodiments, the thermistor may be adhered to the inside surface of the coils of the heater.

A number of electrically conductive paths 884 are run from the base station (not shown) to the proximal end of the device. The electrically conductive paths may carry electrical signals to the piezoelectric tube, the temperature sensor device, and the heater. By way of example, each of four electrically conductive paths 886 may be soldered to or otherwise electrically coupled with respective ones of four, quadrant electrodes on the piezoelectric tube. These four paths may carry drive signals to the piezoelectric tube to cause it to scan the optical fiber, for example in an expanding spiral scan pattern. One conductive path may optionally be provided to a ground electrode inside the piezoelectric tube, although this is not required. Two sensor wires 888 may be electrically coupled with the temperature sensor. Two heater wires 890 may be electrically coupled with the heater. The sensor wires and heater wires may optionally be run along an inner surface of the housing. One or more notches may be provided in the attachment collar at the interface abutting the inner surface of the housing to accommodate passage of these wires.

In one or more embodiments of the invention, wire leading up to the heater may have a higher electrical conductivity than resistive wire or other material of the heater. This may help to reduce resistive losses in areas remote from the scanning optical element. For example, copper wire, such as magnet wire, may lead up to the heater, and the heater may have EVANOHM® nickel-chromium resistance wire, or other wire having a resistance significantly greater than that of copper. The copper or other higher conductivity wire may be soldered to or otherwise coupled with the higher resistance wire. In one aspect, the ends of the copper wire may optionally be electroplated, such as with nickel, or first with nickel and then with gold. Plating with nickel may aid in soldering. Plating with gold may help to reduce oxidation.

The device includes one or more lenses 806. The one or more lenses are positioned in the optical path of light directed through the free end portion of the optical fiber. In one or more embodiments of the invention, the one or more lenses may include lenses from Pentax Corportion, although this is not required.

In one or more embodiments of the invention, optical fibers 892 may be included around the outside of the housing to collect backscattered light from a target surface. By way of example, in the particular case of a full-color scanning fiber endoscope, twelve optical fibers may be included around the outside of the housing for collection of light. The optical fibers may collect and convey light back to photodetectors located at a proximal end of the scanning beam device.

In the description above, for the purposes of explanation, numerous specific details have been set forth in order to provide a thorough understanding of the embodiments of the invention. The particular embodiments described are not provided to limit the invention but to illustrate it. Embodiments may be practiced without some of these specific details. Furthermore, modifications may be made to the embodiments disclosed herein, such as, for example, to the sizes, shapes, configurations, forms, functions, materials, and manner of operation, and assembly and use, of the components of the embodiments. All equivalent relationships to those illustrated in the drawings and described in the specification are encompassed within embodiments of the invention. The scope of the invention is not to be determined by the specific examples provided above but only by the claims below. In other instances, well-known circuits, structures, devices, and operations have been shown in block diagram form or without detail in order to avoid obscuring the understanding of the description.

Elements illustrated in the figures have not necessarily been drawn to scale. For example, the dimensions of some of the elements have been exaggerated relative to others for purposes of illustration. Further, where considered appropriate, reference numerals and/or terminal portions of reference numerals have been repeated among the figures to indicate corresponding or analogous elements, which may optionally have similar characteristics.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention. Accordingly, while the invention has been thoroughly described in terms of several embodiments, those skilled in the art will recognize that the invention is not limited to the particular embodiments described, but may be practiced with modification and alteration within the spirit and scope of the appended claims. The description is thus to be regarded as illustrative instead of limiting.

What is claimed is:

1. An apparatus comprising:
a housing having a transparent portion;
a scanning optical element enclosed within the housing, wherein light is to be directed between the scanning optical element and the transparent portion of the housing, wherein the scanning optical element comprises:
a free end portion of an optical waveguide; and
an actuator to move the free end portion of the optical waveguide;
a temperature adjustment device to adjust a temperature within the housing; and
a temperature sensor device to sense the temperature within the housing.

2. An apparatus comprising:
a housing having a transparent portion;
a scanning optical element enclosed within the housing, wherein light is to be directed between the scanning optical element and the transparent portion of the housing;
a temperature adjustment device to adjust a temperature within the housing; and
a temperature sensor device to sense the temperature within the housing, wherein the apparatus comprises an endoscope.

3. A method comprising inserting an apparatus into a patient, the apparatus comprising:
a housing having a transparent portion;
a scanning optical element enclosed within the housing, wherein light is to be directed between the scanning optical element and the transparent portion of the housing;
a temperature adjustment device to adjust a temperature within the housing; and
a temperature sensor device to sense the temperature within the housing.

4. A method comprising:
sensing a condition of a scanning optical element;
maintaining a temperature of the scanning optical element at a substantially constant value by adjusting a temperature of the scanning optical element in response to the sensed condition;
determining an amount to adjust the temperature by using an algorithm;
scanning light using the scanning optical element; and
reducing distortion in an image constructed using the scanning optical element by said maintaining the temperature of the scanning optical element at the substantially constant value.

5. The method of claim 4, wherein said sensing the condition comprises sensing a condition selected from a temperature and a pressure.

6. The method of claim 4, wherein said adjusting the temperature comprises increasing the temperature by heating.

7. The method of claim 6, further comprising reducing fogging of a transparent material in an optical path of light directed through the scanning optical element by increasing the temperature to value that is not less than a temperature of an environment in which the scanning optical element is deployed.

8. A method comprising:
sensing a condition of a scanning optical element;
maintaining a temperature of the scanning optical element at a substantially constant value by adjusting a temperature of the scanning optical element in response to the sensed condition, wherein said adjusting the temperature comprises increasing the temperature by heating;
reducing fogging of a transparent material in an optical path of light directed through the scanning optical element by increasing the temperature to a value that is not less than a temperature of an environment in which the scanning optical element is deployed, wherein the environment comprises inside a patient, and wherein the temperature ranges from 37-47° C.; and
scanning light using the scanning optical element.

9. A method comprising:
inserting a scanning optical element into a patient;
sensing a condition of the scanning optical element;
maintaining a temperature of the scanning optical element at a substantially constant value by adjusting a temperature of the scanning optical element in response to the sensed condition; and
scanning light using the scanning optical element.

10. The apparatus of claim 1:
wherein the scanning optical element comprises an optical fiber having the free end portion enclosed within the housing and the actuator is to move the free end portion of the optical fiber;
wherein the temperature adjustment device comprises a heater to increase the temperature within the housing in response to the sensed temperature; and
wherein the transparent portion of the housing comprises one or more lenses in an optical path of the light.

11. The apparatus of claim 10, wherein the heater comprises a coil resistance heater coiled around a length of the free end portion of the optical fiber, and wherein the free end portion of the optical fiber is attached to the actuator with an adhesive, and wherein the temperature sensor device is positioned proximate the adhesive.

12. The apparatus of claim 1, wherein the apparatus comprises an endoscope, and further comprising a base station coupled with the endoscope, the base station comprising:
an interface to connect the endoscope;
one or more light sources to provide light to the endoscope through the interface;
an actuator controller to provide a control signals to the endoscope through the interface to control movement of the scanning optical element;
a temperature controller to receive a sensed temperature through the interface, and to provide a control signal to the endoscope through the interface to control the temperature adjustment device to maintain the temperature within the housing at a substantially constant value.

13. The apparatus of claim 1, further comprising a temperature controller in communication with the temperature adjustment device, the temperature controller to provide a control signal to the temperature adjustment device to control the temperature adjustment device to maintain the temperature within the housing at a substantially constant value.

14. The method of claim 4, wherein the scanning optical element comprises an optical fiber attached to a piezoelectric tube with an adhesive, and further comprising maintaining a temperature of the adhesive at a substantially constant value.

15. The apparatus of claim 1, wherein the temperature adjustment device comprises a heater.

16. The apparatus of claim 15, wherein the heater comprises a coil resistance heater.

17. The apparatus of claim 16, wherein the coil resistance heater comprises adjacent loops connected to flow current in opposite direction.

18. The apparatus of claim 16, wherein the coil resistance heater comprises a bifilar coil of a wire that is doubled back on itself.

19. The apparatus of claim 16, wherein the coil resistance heater comprises a greater number of loops per unit length towards one or more ends than towards center.

20. The apparatus of claim 15, wherein the heater comprises a material having an electrical resistance that increases with increasing temperature.

21. The apparatus of claim 15, wherein the heater comprises a thin-film resistance heater.

22. The apparatus of claim 1, wherein the temperature adjustment device comprises a cooler.

23. The method of claim 9, further comprising determining an amount to adjust the temperature by using an algorithm.

* * * * *